(12) United States Patent
Sojka et al.

(10) Patent No.: US 8,058,500 B2
(45) Date of Patent: Nov. 15, 2011

(54) MALODOR REDUCTION PATCH

(75) Inventors: Marci E. Sojka, Neenah, WI (US);
Frederick J. Lang, Neenah, WI (US);
Ann Marie Przepasniak, Sturtevant, WI (US); Tammy J. Balzar, Oshkosh, WI (US); Sarah L. Christoffel, Appleton, WI (US); Kristi Jo Bryant, Appleton, WI (US); Catherine A. Nennig, Neenah, WI (US); Mary F. Kutchenriter, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 349 days.

(21) Appl. No.: 11/297,829

(22) Filed: Dec. 7, 2005

(65) Prior Publication Data
US 2006/0251609 A1  Nov. 9, 2006

Related U.S. Application Data

(60) Provisional application No. 60/678,450, filed on May 6, 2005.

(51) Int. Cl.
*A61F 13/15* (2006.01)
(52) U.S. Cl. .............. 604/359; 604/367; 604/385.02; 604/385.06
(58) Field of Classification Search .......... 604/359, 604/367, 385.02, 385.06
See application file for complete search history.

(56) References Cited

U.S. PATENT DOCUMENTS

| | | | |
|---|---|---|---|
| 3,856,014 A | * | 12/1974 | Yamauchi ............ 604/359 |
| 3,891,584 A | | 6/1975 | Ray-Chaudhuri et al. |
| 4,419,396 A | | 12/1983 | Sugimoto |
| 4,493,869 A | | 1/1985 | Sweeny et al. |
| 4,522,967 A | | 6/1985 | Sheldon et al. |
| 4,600,404 A | | 7/1986 | Sheldon et al. |
| 4,661,388 A | | 4/1987 | Charbonneau |
| 4,720,409 A | | 1/1988 | Spector |
| 4,880,690 A | | 11/1989 | Szycher et al. |
| 5,399,404 A | | 3/1995 | Laughlin et al. |
| 5,678,251 A | | 10/1997 | Getz |
| 5,817,385 A | | 10/1998 | Stanislav |

(Continued)

FOREIGN PATENT DOCUMENTS
EP      0 525 530 A2    2/1993
(Continued)

OTHER PUBLICATIONS

"AROMAPatches®," Internet web page "http://www.aromapatches.com/welcome", Healthwave, Inc., viewed and printed Nov. 20, 2005, 15 pages.

*Primary Examiner* — Jacqueline F. Stephens
(74) *Attorney, Agent, or Firm* — Denise L. Stoker; Randall W. Fieldhack

(57) ABSTRACT

A patch is presented for use in conjunction with a surface, the patch including a backsheet having an adherent surface, wherein the backsheet is translucent; an outermost surface opposite the adherent surface; an adhesive applied to the adherent surface; a peel layer removably attached to the adhesive; and a malodor-reducing agent. A method for manufacturing a patch is presented, the method including producing a backsheet from a water-dispersible polymer; applying a malodor-reducing agent to the polymer; adding an adhesive to the backsheet; and adhering a peel strip to the adhesive.

31 Claims, 5 Drawing Sheets

U.S. PATENT DOCUMENTS

| | | |
|---|---|---|
| 6,159,487 A | 12/2000 | Znaiden et al. |
| 6,162,457 A | 12/2000 | Martz |
| 6,384,297 B1 | 5/2002 | Colman et al. |
| 6,444,761 B1 | 9/2002 | Wang et al. |
| 6,552,162 B1 | 4/2003 | Wang et al. |
| 6,713,140 B2 | 3/2004 | McCormack et al. |
| 6,723,671 B2 | 4/2004 | Zolotarsky et al. |
| 6,808,801 B2 | 10/2004 | George et al. |
| 6,887,961 B2 | 5/2005 | Soerens et al. |
| 2003/0187412 A1 | 10/2003 | Martin |
| 2004/0127866 A1 | 7/2004 | Odorzynski |
| 2005/0089669 A1 | 4/2005 | Sobonya et al. |
| 2005/0124960 A1* | 6/2005 | Ruman .................. 604/385.19 |
| 2006/0194041 A1 | 8/2006 | Mullally et al. |

FOREIGN PATENT DOCUMENTS

| | | |
|---|---|---|
| EP | 0 750 905 A2 | 1/1997 |
| EP | 0980894 * | 2/2000 |
| GB | 2 209 532 A | 5/1989 |
| JP | 09-168583 A | 6/1997 |
| JP | 11-089922 A | 4/1999 |
| JP | 2000-167996 A | 6/2000 |
| WO | WO 95/18191 A1 | 7/1995 |

* cited by examiner

MALODOR REDUCTION PATCH

This application claims priority to provisional application Ser. No. 60/678,450 entitled Malodor Reduction Patch and filed in the U.S. Patent and Trademark Office on May 6, 2005. The entirety of provisional application Ser. No. 60/678,450 is hereby incorporated by reference.

BACKGROUND

This pertains to devices and methods for reducing malodor on or near a surface.

Odor reduction that is attempted using sprays, powders, roll-ons, and sticks tends to be messy, lacking in control of application, and may dissipate rapidly with time. Other attempts at odor reduction include air freshening products that are often larger, heavier decorative devices and/or may require to be plugged into an electrical outlet to function.

SUMMARY

The present invention overcomes the problems by providing aspects of the present invention that allow for easier placement in areas where malodor may be present, that may be made flexible in nature to more readily adapt to different areas/surfaces, that stays in place where put by a user, that does not require an electrical outlet, that is easily removable, and that can easily be replaced to have a new scent.

The present invention provides a patch for use in conjunction with a surface, the patch including a backsheet having an adherent surface, wherein the backsheet is translucent; an outermost surface opposite the adherent surface; an adhesive applied to the adherent surface; a peel layer removably attached to the adhesive; and a malodor-reducing agent.

The present invention also provides a patch for use in conjunction with a surface, the patch including a backsheet having an adherent surface, wherein the backsheet is water-dispersible; an outermost surface opposite the adherent surface; and an adhesive applied to the adherent surface. The patch also includes a peel layer removably attached to the adhesive; an image printed on one of the outermost and adherent surfaces; and a malodor-reducing agent incorporated within the patch.

The present invention also provides a patch for use in conjunction with a surface, the patch including a backsheet having an adherent surface, wherein the backsheet is water-dispersible; an outermost surface opposite the adherent surface; an adhesive applied to the adherent surface; a peel layer removably attached to the adhesive; and a means for reducing malodor.

The present invention also provides a method for manufacturing a patch, the method including producing a backsheet from a water-dispersible polymer; applying a malodor-reducing agent to the polymer; adding an adhesive to the backsheet; and adhering a peel strip to the adhesive.

The present invention also provides a malodor-reducing patch product, the product including a dispenser and a plurality of patches positioned within the dispenser, each patch having a backsheet having an adherent surface, an adhesive applied to the adherent surface, a peel layer removably attached to the adhesive, and a malodor-reducing agent incorporated within the patch.

The present invention also provides a method for selling a malodor-reducing patch, the method including manufacturing a patch having a backsheet having an adherent surface, an adhesive applied to the adherent surface, and a peel layer removably attached to the adhesive; and packaging the patch with an amount of a malodor-reducing agent.

The present invention also provides a method for selling a malodor-reducing patch, the method including producing a patch having a backsheet having an adherent surface, an adhesive applied to the adherent surface, a peel layer removably attached to the adhesive, and a malodor-reducing agent incorporated within the patch. The method also includes manufacturing a feminine hygiene product; and packaging the patch with the feminine hygiene product.

The present invention also includes method for selling a malodor-reducing patch, the method including producing a patch having a backsheet having an adherent surface, an adhesive applied to the adherent surface, a peel layer removably attached to the adhesive, and a malodor-reducing agent incorporated within the patch. The method also includes packaging the patch; and positioning the package in a store adjacent to a feminine hygiene, fragrance, cleaning, furniture, storage, or garment product.

The present invention also provides a patch for use in conjunction with a surface, the patch including a backsheet having an adherent surface, wherein the backsheet is water-dispersible; an outermost surface opposite the adherent surface; an adhesive applied to the adherent surface; a peel layer removably attached to the adhesive; and a malodor-reducing agent.

Objects and advantages of the present invention will become apparent to those skilled in the art in view of the following description and the accompanying drawings.

DETAILED DESCRIPTION OF THE PREFERRED EMBODIMENTS

The term "surface" and its plural generally refer herein to the outer or the topmost boundary of an object.

As used herein, the term "flushable" means that an item may be successfully transported through a toilet and through the typical municipal sewerage system piping and pumps without incident (e.g., clogging).

The term "dispersible" generally refers to a material in which the fibers of that material are capable of debonding or dissolving, resulting in the material breaking down into smaller pieces than the original sheet. Debonding is generally a physical change of scattering or separation. Dissolving is a state change, wherein the material goes into solution, e.g., a water soluble polymer dissolving in water.

The term "water dispersible" generally refers to a fibrous nonwoven composite structure which, when placed in an aqueous environment, will, with sufficient time, break apart or dissolve into smaller pieces. As a result, the structure once dispersed may be more advantageously processible in recycling processes, for example, septic and municipal sewage treatment systems. If desired, such fibrous nonwoven structures may be made more water-dispersible or the dispersion may be hastened by the use of agitation and/or the selection of certain materials as further described below. The actual amount of time will depend at least in part upon the particular end-use design criteria.

The term "launderable" generally refers to objects that largely maintain their structural integrity through a laundry cycle, including washing and drying, without an adverse effect on clothing, washer, or dryer.

The term "translucent" generally refers to permitting the passage of light, both in the sense of being transparent, in which objects may be seen clearly therethrough, and in the sense that light may be transmitted and diffused such that objects are not seen clearly therethrough.

Figure 1:
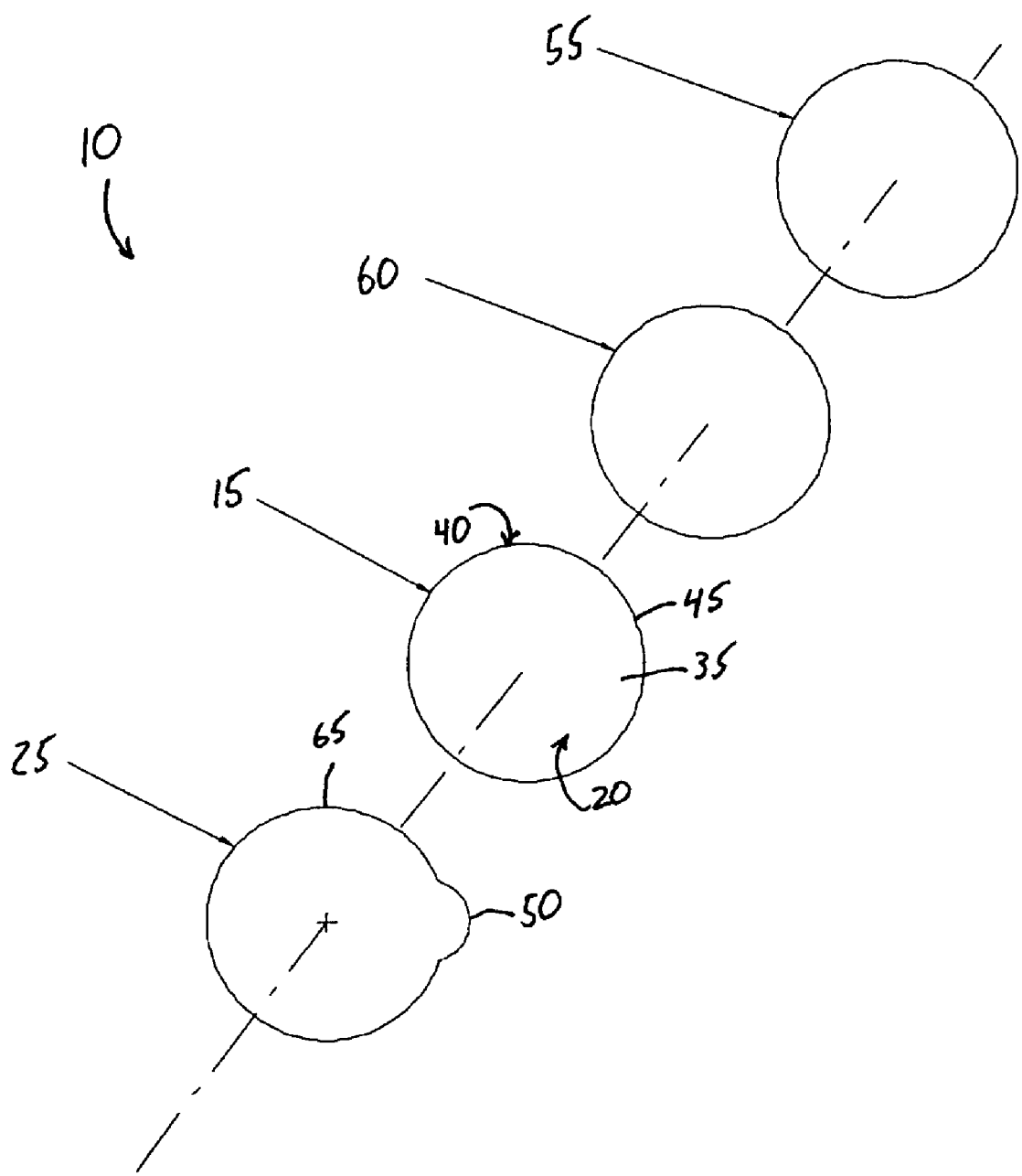
FIG. 1 is an exploded schematic view of a patch of the present invention.

FIG. 1 illustrates an example of a patch 10 as an aspect of the present invention. For purposes of illustration, and not for purposes of limitation, the patch 10 is described as a sticker. The same patch 10, however, may be described as any other suitable form of a patch 10.

The patch 10 includes a backsheet 15, an adhesive 20, a peel layer 25, and a malodor-reducing agent 30. The patch 10 is adapted to be used in conjunction with an undergarment, a garment, an absorbent article, or a drawer, closet, or other storage container for an undergarment, a garment, or an absorbent article. The patch 10 may be used to apply to areas where malodor reduction is desirable. Examples include surfaces such as those in clothing, skin, gym bags, lockers, shoes, trash bags/receptacles, etc. The patch 10 may also be used in conjunction with any article or surface for which, or near which, odor may be an issue. The patch 10 may be constructed to be flexible and soft, particularly for uses on or near a body.

The patch includes a backsheet 15. The backsheet 15 includes an adherent surface 35, an outer surface 40, and a backsheet edge 45. The backsheet 15 is shown as circular, but may be of any suitable shape, including geometric shapes, animal shapes, letter shapes, object shapes, or any other shape. In other aspects of the present invention, the backsheet 15 may be smooth or of various textures as appropriate for the intended use of the patch 10.

In one aspect of the present invention, the backsheet 15 is translucent; a translucent backsheet 15 will allow the patch to be less noticeable when applied to a surface. As an example of a material providing translucency, the backsheet 15 may be manufactured from polyvinyl alcohol (PVA). As a specific example, the PVA may be Gohsenol NK 05 PVOH (71-75% hydrolyzed, 4.5-5.5 mPa-s viscosity). As another specific example, PVA can be combined with ethylene vinyl acetate (EVA) as a processing aid (e.g., 80% PVOH and 20% EVA). In this aspect, the EVA may be Dupont Bynel 3860 maleic anhydride modified EVA. In other aspects of the present invention, the backsheet 15 may also be manufactured from a polymer of polymerized ethylene and acrylic acid, such as polyethylene, polypropylene, polyethylene oxide and ethylene-co-acrylic, or polycaprolactone.

In another aspect of the present invention, the backsheet 15 may include a flushable or water-dispersible material such as those described in co-owned U.S. Pat. Nos. 6,384,297 and 6,713,140. Manufacturing the backsheet 15 from PVA as described above will also provide a water-dispersible backsheet 15 as the PVA is hydrophilic and will break apart upon exposure to water. In another aspect of the present invention, a flushable backsheet 15 may be achieved by manufacturing the backsheet 15 by co-extruding or laminating with polylactic acid (PLA). As a specific example, PLA may be from NatureWorks, LLC, such as their PLA6300 and/or PLA6200.

As another specific example, the PLA may be combined with polylcaprolactone available from, for example, Union Carbide as Tone 767. In other aspects of the present invention, a flushable backsheet 15 may be achieved by manufacturing the backsheet 15 from materials including vinyl alcohol copolymers, polyesters, polyacrylamides, acrylic polymers, vinyl polymers, methacrylic polymers and copolymers, polylactic acid, polycaprolactone, polyester amides, polyhydroxybutyrates, polyester amides, cellulosic derived polymers—hydroxypropyl cellulose, hydroxyalkyl cellulose, polyalkalene oxides, nylon copolymers, acrylic acid copolymers, and polyethylene glycol.

In other aspects of the present invention, any suitable coform, nonwoven, or woven material may be used for the backsheet 15. In one aspect of the present invention, the backsheet 15 is an absorbent material. The backsheet 15 may include a stretch-bonded laminate (SBL) with pre-stretched elastic filament and meltblown material with one ply of spunbond material on each of the adherent and outer surfaces 35, 40 and a basis weight of approximately 70 grams per square meter (gsm), but any suitable nonwoven material may be used.

In other aspects of the present invention, the material chosen for the backsheet 15 may be breathable, or may be made breathable by manufacturing pores in the backsheet 15, so as to be non-occlusive to the skin or other surface contacted by the patch 10.

In other aspects of the present invention, materials for the backsheet 15 may include cotton, rayon, wood pulp, and polymeric substances such as nonwoven fabrics, foam sponges, and thermoplastics. The material maybe formed of a nonwoven fabric that is made of interbonded thermoplastic fibers. The fibers may be formed from a variety of thermoplastic materials including polyolefins (e.g., polyethylene or polypropylene), polystyrene, and polyamides (e.g., nylon). In addition, thermoplastic polymers that are elastomeric may also be used as fibers, including polyurethanes and block copolymers. Blends of any of these materials may be used to form the fibers. The fibers may include additives (e.g., wax, pigments, stabilizers, and fillers) that are inserted as the fibers are fabricated to achieve one or more desired properties within the fibers.

In one aspect of the present invention, materials are chosen to make the backsheet 15 launderable. A launderable backsheet 15 may be formed from a polyethylene film, such as a 1 mil polyethylene film, available from Pliant Corporation, Wisconsin, USA. A launderable backsheet 15 may also be formed from a breathable poly film, such as a 40 gsm breathable poly film, available from Swanson Plastics.

Figure 2:
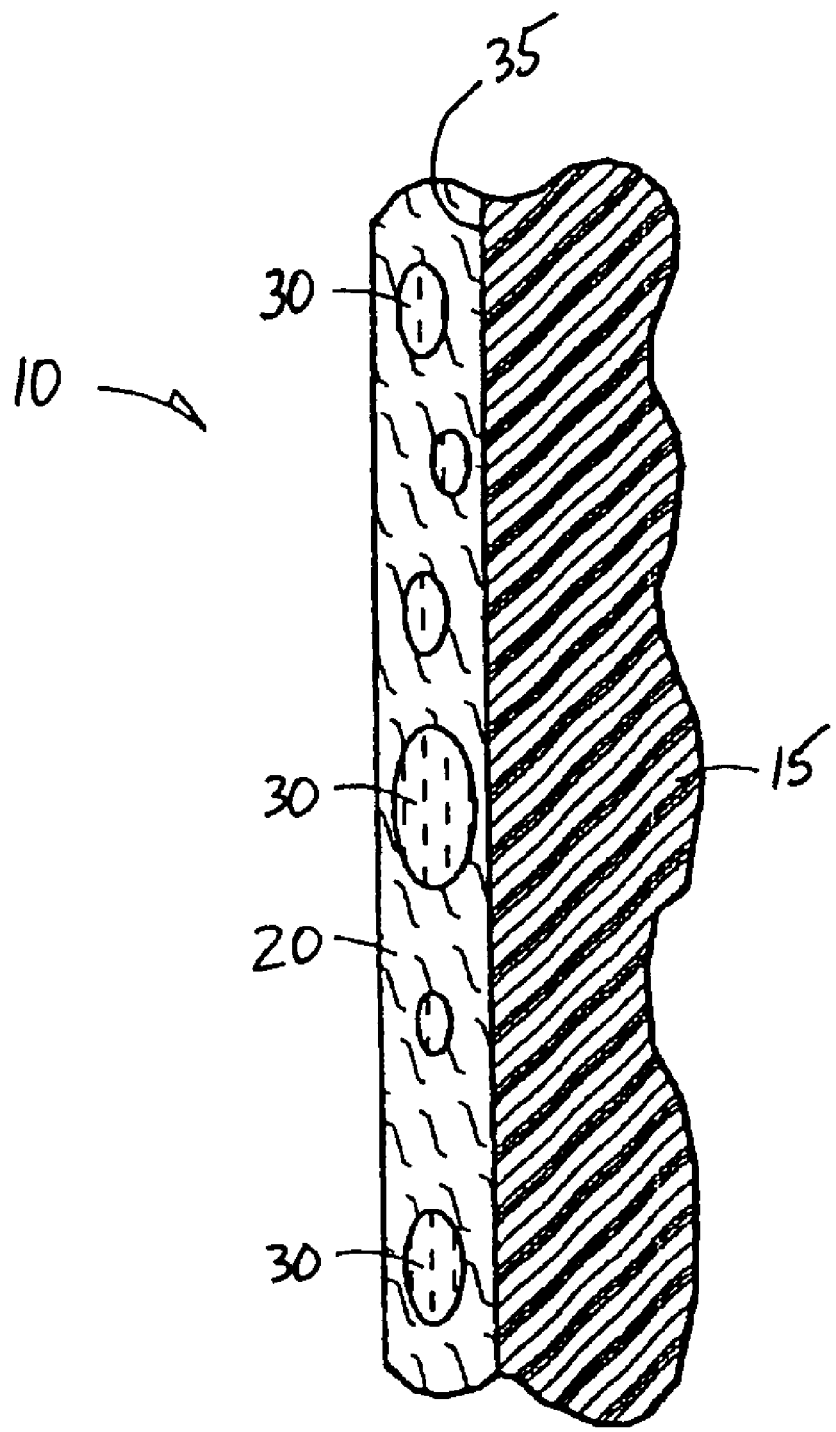
FIG. 2 is a cutaway close-up of a backsheet and adhesive of the patch of FIG. 1.

As illustrated in FIGS. 1 and 2, the patch 10 also includes an adhesive 20 used to removably attach the patch 10 to a surface. The adhesive 20 is applied to the adherent surface 35 of the backsheet 15. The adhesive 20 may be one that will minimize adhesion and detackify once placed in water. In one aspect of the present invention for use in conjunction with garments or container surfaces, the adhesive 20 is 34-5602 block copolymer-based adhesive available from National Starch & Chemical Co., Bridgewater, N.J. Other suitable water-soluble adhesives include those described in U.S. Pat. Nos. 6,444,761; 4,600,404; 4,522,967; and 3,891,584. Patent publication WO 95/181191 also describes water-dispersible adhesive compositions that may be used in an aspect of the present invention.

In other aspects of the present invention, the adhesive 20 may be EVA, polyolefins, starches, styrenic block copolymers (SBC), natural rubber, polybutylene, acrylics, polyurethanes, epoxies, polyesters, polyamides, and silicones. The adhesive 20 may also be a hot-melt adhesive including EVA, SBC, or amorphous poly-alpha-olefin (APAO). The adhesive 20 may also be a synthetic adhesive such as an emulsion-based formula (e.g., poly vinyl acetate (PVAc), EVA, and rubber including styrene-butadiene rubber and neoprene) or a solution-based formula (e.g., PVA, KYMENE polyamideepichlorohydrin (PAE) resin available from Hercules, and polyethylene oxide). The adhesive 20 may be a water-based adhesive including either or both natural or synthetic ingredients including polymers, thickeners, fillers, tackifiers, humectants, and wetting enhancers. The adhesive 20 may also be a natural adhesive including starches such as corn, tapioca, and wheat, and such things as dextrin and animal glue. The adhesive 20 may also be an adhesive binder including acrylic, ethylene ethyl, acrylate, PVAc, EVA, PVA, cellulose acetate, polyethylene, polypropylene, polyester, or poly vinyl chloride (PVC). In other aspects of the present invention, the adhesive 20 may be any other adhesive suitable for removably attaching the patch to the intended surface.

In still another aspect of the present invention for use in conjunction with a skin surface, the adhesive 20 may be chosen to be a skin-friendly medically-approved body adhesive. In other aspects of the present invention, the adhesive 20 may be patterned on the patch 10 to ease removal of the patch. For example, the adhesive 20 may be applied in a scalloped pattern, in a star pattern, in a circle smaller than the size of the patch 10, or in any other suitable pattern. In another aspect of the present invention, the amount of adhesive 20 applied to the patch 10 may in a gradient to provide greater resistance to removal in one or more portions of the patch 10.

Returning to FIG. 1, the patch 10 also includes a peel layer 25 removably attached to the adhesive 20 to prevent the adhesive 20 from sticking to other than the intended surface. The peel layer 25 is generally sized and shaped to match the size and shape of the backsheet 15 or the adhesive 20. In another aspect of the present invention, the peel layer 25 may includes a tab 50 extending beyond the edge 45 of the backsheet 15 in a radially-outward direction to facilitate removal of the peel layer 25 from the backsheet 15 prior to use of the patch. In one aspect of the present invention, the peel layer 25 may be silicone-treated paper. For example, Tekkote 24 KSA 24# Peel Release including OTIS 6146 paper coated on one side with silicone release formulation with control release additive, supplied by Tekkote Corporation, New Jersey, USA, may be used. In another aspect of the present invention, the peel layer 25 may be a flushable construction including a paper base sheet with a water-soluble binder (PVOH) and a silicone release coating. Material for such a peel layer 25 is available from Sansei E&M, Japan and from International Paper, Wisconsin, USA. The peel layer 25 may also be a thin layer of release coating on a water soluble film.

In one aspect of the present invention, the patch 10 may also include a cover sheet 55. The cover sheet 55 is attached to the outer surface 40 of the backsheet 15 using a construction adhesive. In this aspect, the surface of the cover sheet 55 not attached to the backsheet 15 becomes the outermost surface of the patch 10. In one aspect of the present invention, the cover sheet 55 may be made from rayon and polyethylene terephthalate (PET). A specific example of a material used for the cover sheet 55 is an 85 gsm hydroentangled spunlace, 70 mm slit width, available from Fujian Nanfang Textile Co., Sandler, Germany. In other aspects of the present invention, the cover sheet 55 may be made from the same variety of materials and material combinations as that for the backsheet 15 material as described above. When the cover sheet 55 is used in conjunction with a backsheet 15, the material of the cover sheet 55 may be more breathable than the material of the backsheet 15. The material of the cover sheet 55 may be left untreated, or the material may be treated to alter its original hydrophilic/hydrophobic properties.

In another aspect of the present invention, the peel layer 25 may include a tab 50 attached to the peel layer 25 at other than a peel layer edge 65 of the peel layer 25. The tab 50 may be a semi-circular extension attached to the peel layer 25 along a diameter of the peel layer 25. The tab 50 may also be attached to any position on the peel layer 25 and folded down to be generally coplanar with the peel layer 25 such that a user may pry up the tab 50 and then use the tab 50 to remove the peel layer 25 from the patch 10.

In other aspects of the present invention, the cover sheet 55 may be attached to the backsheet 15 through the use of adhesives, pressure, heat, ultrasonics, hook material or other mechanical or chemical means. In one aspect of the present invention, the construction adhesive used to attach the cover sheet 55 to the backsheet 15 is an Easy Melt #34-5610 construction adhesive available from National Starch. In other aspects of the present invention, the adhesives described above for use as the adhesive 20 may also be used to attach the cover sheet 55 to the backsheet 15. In addition, the construction adhesive used to attach the cover sheet 55 could be water-soluble or include a bonding process that is water-soluble (e.g., polymers, binders, etc.). Examples of soluble or delayed dispersible materials include binder compositions with components described in co-pending and commonly-owned U.S. patent application Ser. Nos. 10/427,809 Absorbent Binder Composition And Method Of Making It and 10/427,808 Absorbent Article With Self-Forming Absorbent Binder Layer. Suitable binder compositions include those with a crosslinked absorbent polymer and a dispersion agent added in an amount so as to maintain structural integrity in the product during use. Such dispersion agent may be present in an amount such that the product loses structural integrity at some point, whether instantly or within a given time of immersion in water. In addition, any suitable adhesive may be used to attach the cover sheet 55 to the backsheet 15.

In one aspect of the present invention, the patch 10 may also include a scent pad 60 interposed between the backsheet 15 and the cover sheet 55. The scent pad 60 is merely a carrier sheet for the malodor-reducing agent 30. This scent pad 60 could be a carrier for a fragrance, an odor absorbing material, odor neutralizer, color change indicator, etc. This scent pad 60 could absorb moisture such as that from skin, perspiration, menses, urine, dirt, etc. In one aspect of the present invention, the scent pad 60 is made from rayon and PET or from starch. In other aspects of the present invention, the scent pad 60 may be made from any suitable material that has been described for use in manufacturing either the cover sheet 55 or the backsheet 15.

In other aspects of the present invention, the patch 10 may incorporate features, structures, and materials described in co-pending and commonly-owned U.S. patent application Ser. No. 11/069,318 Device for Releasing an Agent to be Detected Through Olfaction, incorporated herein by reference.

The patch 10 also includes a malodor-reducing agent 30. The malodor-reducing agent 30 may be incorporated into the patch in a number of locations, by a number of methods, and with a number of release mechanisms. A means for reducing malodor includes any combination of the factors described below.

The malodor-reducing agent 30 may be manufactured into the material used to make the backsheet 15, the cover sheet 55, the scent pad 60, the peel layer 25, or the adhesive 20. The backsheet 15, scent pad 60, or cover sheet 55 may be manufactured by extruding a polymer to form the material from which each of these is made. In one aspect of the present invention, the malodor-reducing agent 30 is applied to, or mixed into, the polymer prior to extruding the polymer. In another aspect of the present invention, the malodor-reducing agent 30 is applied to the polymer after extruding the polymer. In still another aspect of the present invention, the malodor-reducing agent 30 is encapsulated and then added to the polymer. In another aspect of the present invention, the malodor-reducing agent 30 is sprayed onto the polymer. In other aspects of the present invention, the malodor-reducing agent 30 is printed on or similarly applied to the polymer, on the cover sheet 55, scent pad 60, or backsheet 15, or on the packaging, pouch, container, or tissue that encloses or packages the patch 10.

In other aspects of the present invention, the malodor-reducing agent 30 may be applied to either or both of the peel layer 25 and the adhesive 20 such that the malodor-reducing agent 30 is released when the peel layer 25 is peeled away from the adhesive 20, or the malodor-reducing agent 30 may be formulated with the adhesive 20 and applied to the backsheet 15 or the peel layer 25. The malodor-reducing agent 30 may also be in an encapsulated form within the adhesive 20 and may activate upon contact with the backsheet 15 or the peel layer 25 during the manufacturing process.

In other aspects of the present invention, the malodor-reducing agent 30 may be provided such that it will release from the patch 10 in a time-release manner. This may be accomplished through micro-encapsulation of the malodor-reducing agent 30. This may also be accomplished by using a malodor-reducing agent 30 that is heat-triggered, moisture-triggered, perspiration-triggered, pressure-triggered, or chemically-triggered.

In one aspect of the present invention, the malodor-reducing agent 30 is a fragrance used to mask a malodor. Example fragrance oils include Dandelion Breeze w/ Jasmine available from Givaudan, Totally T with Aloe available from Givaudan, Soothing available from Firmenich, and Chamomile Dreams available from Symrise.

In another aspect of the present invention, the malodor-reducing agent 30 may be an odor neutralizer or absorber to assist in eliminating a malodor. Materials able to neutralize and/or absorb odors include nanoparticles, activated carbon, zinc and aluminum oxides, zeolites, acid-based neutralization (e.g., lemon juice), clays, and other sequestrants.

The malodor-reducing agent 30 may be a bioactive fragrance such as a fragrance that destroys bacteria or a fragrance that both masks and removes odors.

In another aspect of the present invention, the malodor-reducing agent 30 may be a combination of one or more fragrances, odor neutralizer/absorbers, or other suitable agents.

In one aspect of the present inventions, the patch 10 may include an image printed or otherwise established on the patch 10. The image may be any drawing, photograph, graphic, logo, or trademarked image. The image may be printed on or otherwise applied to the cover sheet 55, the scent pad 60, or the backsheet 15. In another aspect of the present invention, the image may be linked to the branding for the product.

In another aspect of the present invention, the malodor-reducing agent 30 may be blended with the ink or other substance used to print or otherwise apply the image to the patch 10. This aspect can be achieved through use of encapsulated fragrance oil that is stable and compatible with the ink chemistry. In still another aspect of the present invention, the ink or other substance used in producing the image may change color with time or with another factor.

In another aspect of the present invention, the patch 10 may include an odor indicator to indicate to the user of the patch 10 that a new patch 10 may be needed. In other aspects of the present invention, the patch 10 may include a time, temperature, or moisture indicator to indicate to the user of the patch 10 that a new patch 10 may be needed. As an example of a patch 10 with a temperature indicator, the materials used to manufacture the patch 10 can be made by adding ingredients such as a thermochromic pigment (such as those used in microencapsulated leuco dyes) or one or more polythiopenes directly before extrusion of polyethylene, polypropylene, PET, polyester, or other thermoplastic films. The patch 10 may be manufactured to include a time or moisture indicator by adding a wicking strip with colored dyes.

Figure 3:
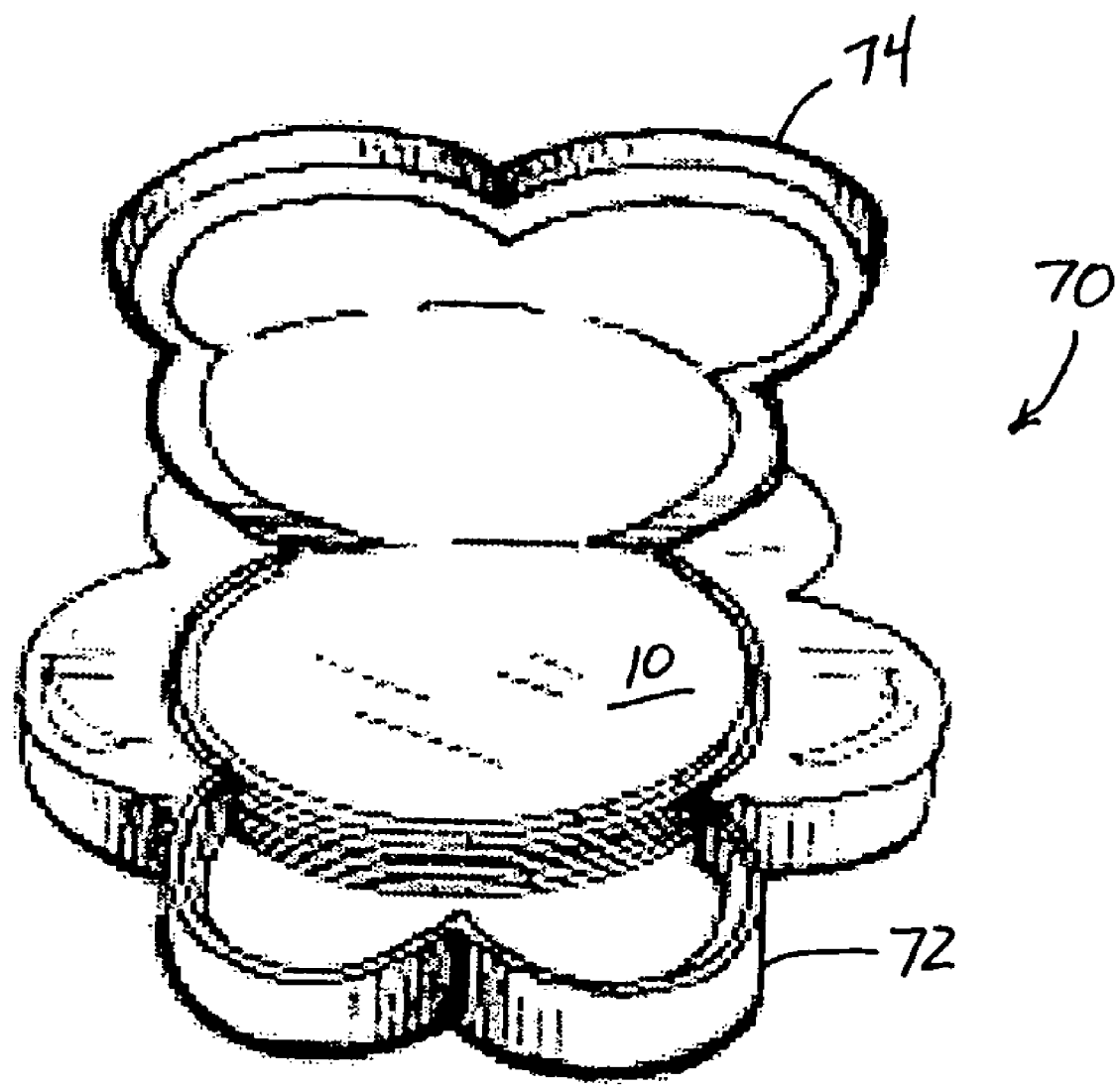
FIG. 3 is a perspective view of a container for the patch of FIG. 1.
Figure 4:
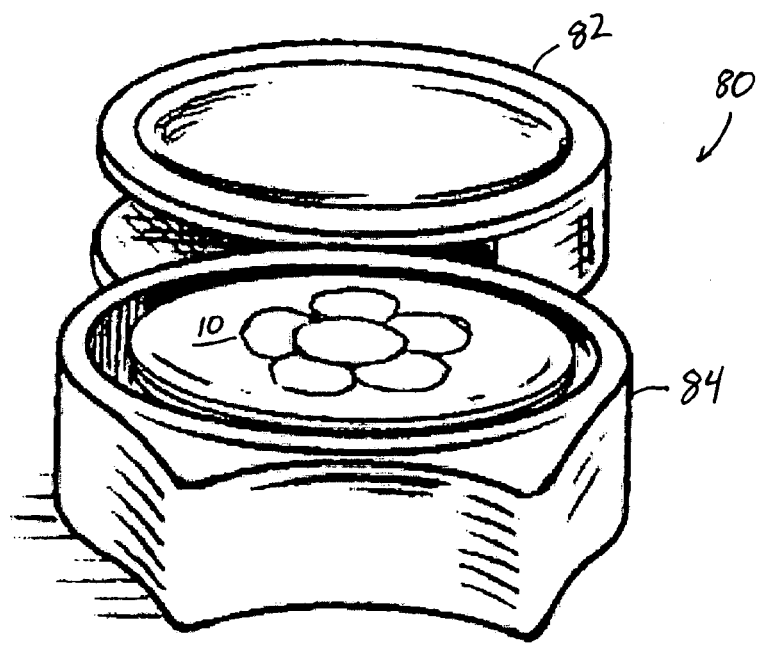
FIG. 4 is a perspective view of an alternate container for the patch of FIG. 1.
Figure 5:
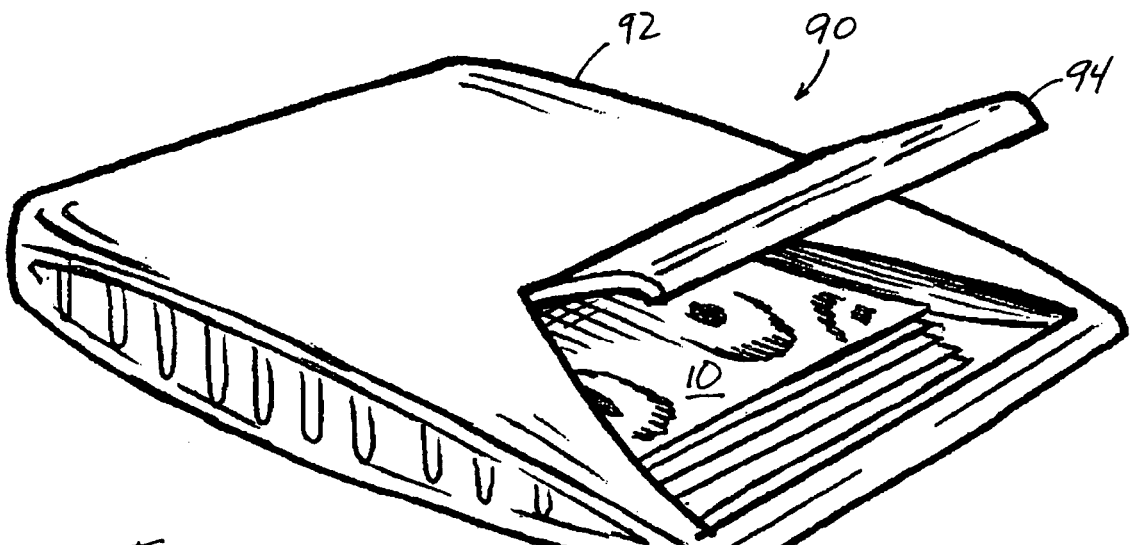
FIG. 5 is a perspective view of an alternate container for the patch of FIG. 1.
Figure 6:
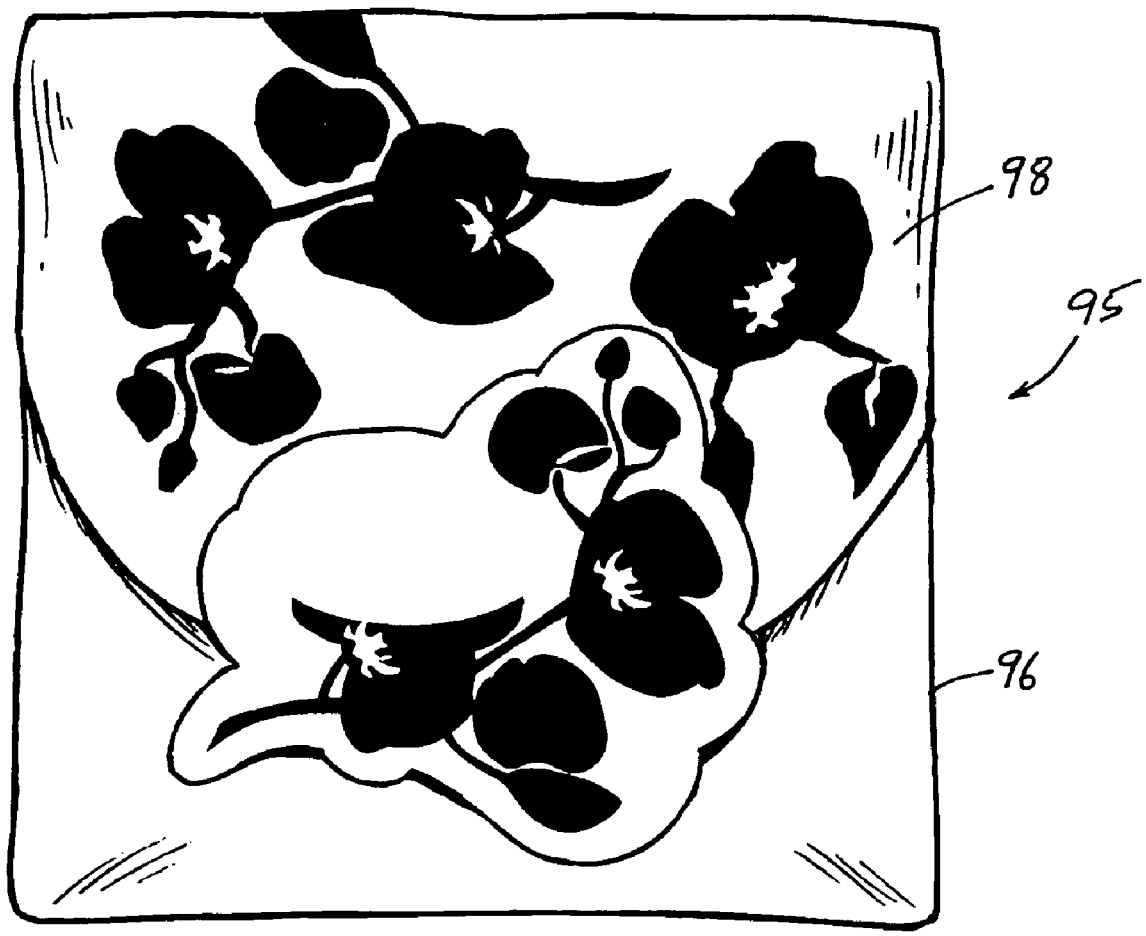
FIG. 6 is a plan view of an alternate container for the patch of FIG. 1.

The patches 10 may be delivered to a user in a number of ways. In one aspect of the present invention, one or more patches 10 may be assembled and placed in a portable dispenser such as a compact 70 (see FIG. 3). In one aspect of the present invention, the compact is a flip-open compact having a base 72 and a cover 74, in which the patches 10 are accessed by opening the cover 74. In another aspect of the present invention, the dispenser is a slide-out compact 80 (see FIG. 4) having a shell 82 and a receiver 84, in which the patches 10 are held primarily within the receiver 84 and are accessed by sliding or rotating the receiver 84 out from within the shell 82. In another aspect of the present invention, the dispenser is a snap-open compact 90 (see FIG. 5) with a housing 92 and a door 94. The patches 10 are held primarily within the housing 92 and are accessed by snapping open the door 94. In another aspect of the present invention, the dispenser is a pouch 95 (see FIG. 6) with an envelope 96 and a flap 98. The patches 10 are held primarily within the envelope 96 and are accessed by opening the flap 98.

In other aspects of the present invention, the peel layer 25 may be made large enough to accommodate a plurality of patches 10 in a one-dimensional or two-dimensional array. A one-dimensional array may be arranged as a strip or as a roll, and a two-dimensional array may be arranged on a sheet or as a roll. In any of these aspects, the peel layer 25 may also be perforated between patches 10 for ease of separation from the remaining strip, sheet, or roll. In any of these aspects, the strip, sheet, or roll may be placed in a dispenser.

In another aspect of the present invention, one or more patches 10 manufactured without a malodor-reducing agent 30 may be packaged and provided to a user such that the user may provide and apply the user's own malodor-reducing agent 30, such as a favorite fragrance. Such a packaging may include instructions instructing the user in the method for using such patches 10. In another aspect of the present invention, an amount of one or more malodor-reducing agents 30 in spray bottles, pouches, packets, or in any other suitable containers may be packaged in a kit with such patches 10 to allow a user to add a malodor-reducing agent 30 to the patches 10 in an amount and in a timing as desired by the user. The malodor-reducing agent 30 in this aspect may be a fragrance, including a trademarked fragrance or a commercially-popular fragrance. The user may be able to mix and match fragrances to customize the malodor-reducing agent 30.

In other aspects of the present invention, the patch 10 may used as a tester substrate in a retail cosmetics/fragrance environment, as a portable perfume applicator, and as a deodorant.

In another aspect of the present invention, the patch 10 may be distributed by packaging the patch 10 with a feminine hygiene product, a garment, an undergarment, furniture, storage containers, cleaners, air fresheners, or with any other suitable product. Such packaging may be performed by a manufacturer of feminine hygiene products, by a distributor of such products, or by any other suitable party.

In still another aspect of the present invention, the patch 10 may be distributed by packaging one or more patches 10, and then positioning the package of one or more patches 10 in a store adjacent to a feminine hygiene product, a garment, an undergarment, furniture, storage containers, cleaners, air fresheners, or with any other suitable product.

In another aspect of the present invention, a user may be supplied with a patch 10 having no image thereon. The user may then print an image using an inkjet or other suitable printer.

In another aspect of the present invention, the dispenser for the product may dispense the patches 10 one at a time by pulling one out the dispenser, causing the next patch to move in position to be dispensed, similarly to a dispenser of razor blades. The patches may also be dispensed one at a time by moving a lever, similarly to a dispenser of PEZ-brand candy.

In use, a user obtains a patch 10. If the patch 10 is provided in a package or a compact, the user removes a patch 10 from the package or compact. The user then removes the peel layer 25 from the patch 10, and applies the patch 10 to an undergarment, a garment, an absorbent article, or a drawer, closet, or other container, or to any other surface for which or near which odor may be an issue. If the backsheet 15 of the patch 10 is made from a water-dispersible material, and the user applies such patch 10 to a washable garment, the user may then launder the garment, during which the backsheet 15 will disperse, leaving no trace of the patch 10 on the garment.

EXAMPLE 1

In an example of an aspect of the present invention, a number of launderable patches 10 were manufactured. The backsheet 15 was formed from a 40 gsm breathable poly film, 68 mm width, available from ZiHua Shanghai, Swanson. The cover sheet 55 was formed from an 85 gsm hydroentangled spunlace, 70 mm slit width, available from Fujian Nanfang Textile Co., Sandler, Germany. The backsheet 15 was attached to the cover sheet 55 using an Easy Melt #34-5610 construction adhesive available from National Starch. Adhesive 20 in the form of Dispomelt #570-5504, available from National Starch, was applied to the adherent surface 35 of the backsheet 15. A peel layer 25 made from basic paper with blue printing, basis wt 45 gsm, 66 mm width, available from Jiangshu Taoshi Paper Company, was attached to the adhesive 20 on the adherent surface 35. Each of the fragrances Dandelion Breeze w/ Jasmine available from Givaudan, Totally T with Aloe available from Givaudan, Soothing available from Firmenich, and Chamomile Dreams available from Symrise, was applied to a patch 10. Each completed patch 10 was applied to a garment after removing the peel strip from the patch 10.

EXAMPLE 2

In an example of an aspect of the present invention, a number of launderable patches 10 were manufactured. A launderable backsheet 15 was formed from a 1 mil polyethylene film, 68 mm width, available from Pliant Corporation, Wisconsin, USA. The cover sheet 55 was formed from 0.4 osy spunbond, 70 mm slit width, available from Kimberly-Clark Corporation, Wisconsin, USA. The backsheet 15 was attached to the cover sheet 55 using an Easy Melt #34-5610 construction adhesive available from National Starch. Adhesive 20 in the form of Easy Melt #34-5602, available from National Starch, was applied to the adherent surface 35 of the backsheet 15. A peel layer 25 made from coextruded polypropylene peel strip, 66 mm width, available from Huthamaki, was attached to the adhesive 20 on the adherent surface 35. A Firmenich Fresh Linen fragrance was applied to a patch. Each completed patch 10 was applied to a garment after removing the peel strip from the patch 10.

EXAMPLE 3

In an example of an aspect of the present invention, a number of launderable patches 10 were manufactured. A launderable backsheet 15 was formed from a 40 gsm breathable poly film, 68 mm width, available from Swanson Plastics. The cover sheet 55 was formed from a printable 0.6 osy SMS, available from Kimberly-Clark. The backsheet 15 was attached to the cover sheet 55 using an Easy Melt #34-5610 construction adhesive available from National Starch. Adhesive 20 in the form of Easy Melt #34-5602, available from National Starch, was applied to the adherent surface 35 of the backsheet 15. A peel layer 25 made from basic paper, basis weight of 45 gsm, available from Tekkote, was attached to the adhesive 20 on the adherent surface 35. Each of the fragrances Dandelion Breeze with Jasmine available from Givaudan, Totally T with Aloe available from Givaudan, Soothing available from Firmenich, Fresh Linen available from Firmenich, and Chamomile Dreams available from Symrise, was applied to a patch 10. Each completed patch 10 was applied to a garment after removing the peel strip from the patch 10.

EXAMPLE 4

In an example of an aspect of the present invention, a number of dispersible patches 10 were manufactured. The backsheet 15 was formed from a blend of polyethylene oxide and ethylene-co-acrylic acid in a weight ratio of about 80/20, available from Planet Technologies, California, USA. The cover sheet 55 was formed from PVA available from Gohsenol and EVA available from Dupont. The backsheet 15 was attached to the cover sheet 55 using a #34-731A water soluble construction adhesive available from National Starch. Adhesive 20 in the form of Easy Melt #34-5602, available from National Starch, was applied to the adherent surface 35 of the backsheet 15. A peel layer 25 made from coextruded polypropylene peel strip, 66 mm width, available from Huthamaki, was attached to the adhesive 20 on the adherent surface 35. A Firmenich Fresh Linen fragrance was applied to a patch. Each completed patch 10 was applied to a garment after removing the peel strip from the patch 10.

Embodiments of the invention have been described with reference to various specific and illustrative aspects and techniques. However, it should be understood that many variations and modifications may be made while remaining within the spirit and scope.

Accordingly, this is intended to embrace all such alternatives, modifications and variations that fall within the spirit and scope of the appended claims.

We claim:

1. A patch for use in conjunction with a surface, the patch comprising:
a backsheet having an adherent surface, wherein the backsheet is translucent, and wherein the backsheet comprises one or more materials selected from the group consisting of polyethylene, polypropylene, maleic anhydride, and polyethylene oxide;
an outermost surface opposite the adherent surface, the outermost surface comprising a cover sheet;

an adhesive applied to the adherent surface;

a peel layer removably attached to the adhesive; and a malodor-reducing agent comprising a fragrance, the malodor reducing agent is incorporated into a scent pad located between the backsheet and the outermost surface.

2. The patch of claim 1, wherein the malodor-reducing agent is incorporated into the backsheet.

3. The patch of claim 1, wherein the malodor-reducing agent is incorporated into the adhesive.

4. The patch of claim 1, wherein the malodor-reducing agent comprises an odor absorber.

5. The patch of claim 1, wherein the backsheet is water-dispersible.

6. The patch of claim 5, wherein the backsheet includes polyvinyl alcohol.

7. The patch of claim 5, wherein the backsheet includes polyvinyl alcohol with polylactic acid.

8. The patch of claim 1, wherein the backsheet has an edge, and wherein the peel layer includes a tab extending radially outward beyond the edge.

9. The patch of claim 1, wherein the backsheet is manufactured from an extruded malodor-reducing-agent-containing polymer.

10. The patch of claim 1, wherein the surface is skin.

11. The patch of claim 1, wherein the surface is fabric.

12. The patch of claim 1, wherein the surface is a bathroom surface.

13. The patch of claim 1, further comprising an indicator.

14. The patch of claim 13, wherein the indicator indicates one of time, temperature, and moisture.

15. The patch of claim 1, wherein the adhesive is translucent.

16. A patch for use in conjunction with a surface, the patch comprising:
- a backsheet having an adherent surface, wherein the backsheet is water-dispersible, and wherein the backsheet comprises one or more materials selected from the group consisting of polylactic acid and polylcaprolactone;
- a cover sheet having an outermost surface, the cover sheet opposite the adherent surface;
- a scent pad located between the cover sheet and the back sheet;
- an adhesive applied to the adherent surface;
- a peel layer removably attached to the adhesive;
- an image printed on one of the outermost and adherent surfaces; and
- a malodor-reducing agent comprising a fragrance incorporated within the patch.

17. The patch of claim 16, wherein the malodor-reducing agent is a fragrance.

18. The patch of claim 16, wherein the image is a trademarked image.

19. The patch of claim 16, wherein the cover sheet is translucent.

20. The patch of claim 16, wherein the scent pad is translucent.

21. The patch of claim 16, wherein the backsheet is translucent.

22. The patch of claim 16, wherein the adhesive is translucent.

23. A method for manufacturing a patch, the method comprising:
- producing a backsheet from a water-dispersible polymer comprising one or more materials selected from the group consisting of polylactic acid and polylcaprolactone;
- producing a scent pad for attachment to the backsheet;
- producing a cover sheet for covering the scent pad;
- applying a malodor-reducing agent to the polymer;
- adding an adhesive to the backsheet; and
- adhering a peel strip to the adhesive.

24. The method of claim 23, further comprising extruding the polymer.

25. The method of claim 23, wherein the malodor-reducing agent is applied to the polymer prior to extruding the polymer.

26. The method of claim 25, wherein the malodor-reducing agent is applied to the polymer after extruding the polymer.

27. The method of claim 23, wherein applying the malodor-reducing agent further comprises adding capsules of the malodor-reducing agent to the polymer.

28. The method of claim 23, wherein applying the malodor-reducing agent further comprises spraying the malodor-reducing agent on the polymer.

29. The method of claim 23, wherein applying the malodor-reducing agent further comprises printing the malodor-reducing agent on the polymer.

30. The method of claim 23, wherein the backsheet is translucent.

31. A method for selling a malodor-reducing patch, the method comprising:
producing a patch having:

a backsheet having an adherent surface, wherein the backsheet is translucent, and wherein the backsheet comprises one or more materials selected from the group consisting of polyethylene, polypropylene, maleic anhydride, and polyethylene oxide;
- an outermost surface opposite the adherent surface, the outermost surface comprising a cover sheet;
- an adhesive applied to the adherent surface;
- a peel layer removably attached to the adhesive; and
- a malodor-reducing agent comprising a fragrance, the malodor reducing agent is incorporated into a scent pad located between the backsheet and the outermost surface;

manufacturing a feminine hygiene product; and packaging the patch with the feminine hygiene product.

* * * * *